United States Patent [19]

Alexander et al.

[11] Patent Number: 5,227,374

[45] Date of Patent: * Jul. 13, 1993

[54] LYOPHILIZED CYCLOPHOSPHAMIDE

[75] Inventors: Robert L. Alexander; Robert J. Bequette; Terry T. Kensler; Joseph A. Scott, all of Evansville, Ind.

[73] Assignee: Mead Johnson & Company, Evansville, Ind.

[*] Notice: The portion of the term of this patent subsequent to Aug. 27, 2002 has been disclaimed.

[21] Appl. No.: 812,155

[22] Filed: Dec. 23, 1991

Related U.S. Application Data

[63] Continuation of Ser. No. 709,744, Mar. 8, 1985, which is a continuation of Ser. No. 589,202, Mar. 13, 1984, Pat. No. 4,537,883, which is a continuation-in-part of Ser. No. 440,906, Nov. 12, 1982, abandoned.

[51] Int. Cl.$^5$ ............... A61K 31/66; A61K 33/00
[52] U.S. Cl. ................... 514/110; 514/960; 424/487
[58] Field of Search ............... 514/110, 960; 424/489

[56] References Cited

U.S. PATENT DOCUMENTS

| | | | |
|---|---|---|---|
| 3,018,302 | 1/1962 | Arnold et al. | 260/936 |
| 3,608,077 | 9/1971 | Ginsig | 514/178 |
| 3,732,340 | 5/1973 | Arnold et al. | 260/936 |
| 3,931,409 | 1/1976 | Nickel et al. | 514/538 |
| 4,277,475 | 7/1981 | Vickery | 514/399 |
| 4,537,883 | 8/1985 | Alexander et al. | 514/960 |
| 5,130,305 | 7/1992 | Palepu et al. | 514/110 |

OTHER PUBLICATIONS

Brooke, et al., American Journal of Hospital Pharmacy, 32:44-45 (1975).
Lachman, et al., "The Theory and Practice of Industrial Pharmacy", 2nd Ed., Lea & Febiger, Philadelphia, Pa., pp. 521-524 (1976).
Anon, "Remington's Pharmaceutical Sciences", 15th Ed., Mack Publishing Co., Easton, Pa., pp. 1483-1485 (1975).

Primary Examiner—Nathan M. Nutter
Attorney, Agent, or Firm—Kenyon & Kenyon

[57] ABSTRACT

A lyophilized pharmaceutical solid composition containing cyclophosphamide for reconstitution with water to provide a solution for oral or parenteral administration. This lyophilized cyclophosphamide solid composition demonstrates improved stability, solubility characteristics and enhanced appearance compared with currently available dry powder pre-mix compositions of cyclophosphamide. The lyophilized solid composition contains about 20 parts by weight of cyclophosphamide, about 1½-2 parts by weight of water and from about 10-85 parts by weight of excipient which is comprised mainly of mannitol. Processes for making the composition are disclosed.

2 Claims, No Drawings

LYOPHILIZED CYCLOPHOSPHAMIDE

CROSS REFERENCE TO RELATED APPLICATION

This is a continuation of application Ser. No. 06/709,744 filed Mar. 8, 1985, which is a continuation of application Ser. No. 06/589,202 filed Mar. 13, 1984, now U.S. Pat. No. 4,537,883, which is a continuation-in-part application of Ser. No. 06/440,906 filed Nov. 12, 1982 and now abandoned.

BACKGROUND OF THE INVENTION

Cyclophosphamide is the generic name for 2-[bis(2-chloroethyl)amino]tetrahydro-2H-1,3,2-oxazaphosphorine-2-oxide monohydrate, a widely used antineoplastic drug chemically related to the nitrogen mustards. Cyclophosphamide was one example of a group of novel cyclic phosphoric acid ester amides which were disclosed and claimed in U.S. Pat. No. 3,018,302 granted Jan. 23, 1962 to H. Arnold, et al.

A related series of compounds bearing substituents on the oxazaphosphorine ring nitrogen was disclosed and claimed in U.S. Pat. No. 3,732,340 granted May 8, 1973 also to H. Arnold, et al.

Over the past 20 years a considerable amount of literature concerning cyclophosphamide has accumulated. Most of these references deal mainly with clinical applications of this agent as an antineoplastic drug. Cyclophosphamide has been distributed for much of that time by Mead Johnson & Company under the proprietary name CYTOXAN®. ENDOXAN®' and NEOSAR® are proprietary names for similar pharmaceutical formulations of cyclophosphamide which are essentially comparable to CYTOXAN®.

While cyclophosphamide comprises the monohydrate drug form, which is the easiest to isolate and with which to work, the anhydrous form also exists. No other hydrate form has been reported. As used herein, the term "cyclophosphamide" refers generically to the drug substance (i.e., either the monohydrate or the anhydrous form) the term "cyclophosphamide monohydrate" refers specifically to the monohydrate and the term "anhydrous cyclophosphamide" refers to the anhydrous form. The monohydrate form is preferred for pharmaceutical processing, as the anhydrous form readily picks up water to form the monohydrate when exposed to a relative humidity of about 20–30% or higher at about 25° C. While the monohydrate is stable, nonetheless, under dry conditions (relative humidities of about 20% or less) the monohydrate begins to lose this water of hydration which can cause problems in manufacture. Because of stability limitations which may be due in part to ready interconversion between the anhydrous and monohydrate forms, it is recommended that storage temperatures for cyclophosphamide products not exceed 30° C. (86° F.), and preferably be stored at about 25° C. (77° F.).

Currently, the parenteral dosage formulations of cyclophosphamide consist of sterile packaged dry powder blend admixtures of cyclophosphamide monohydrate and sodium chloride. These premixes are dissolved in water prior to administration which can be oral as well as parenteral. It is intended that the solution itself be administered promptly after being prepared but it is satisfactory for use up to several hours after preparation. During processing and/or storage of the present dry powder premix formulation, a glassiness and/or stickiness can be acquired by the premix composition giving an unattractive material with inferior solubility characteristics and decreased potency. This deterioration is more pronounced as storage time is extended or if the upper limit of the storage temperature range is exceeded.

A common practice used with constitution of sterile solids by a suitable aqueous vehicle consists of warming the container to expedite the dissolution process, especially when the solids dissolve slowly. A study examining the effect of briefly heating cyclophosphamide solutions was reported by D. Brooke, et al. in *American Journal of Hospital Pharmacy*, 32:44–45 (1975). This study concluded that warming vials of cyclophosphamide in order to facilitate dissolution after adding an aqueous vehicle could decrease the potency of the final injectable product. In summary, these stability limitations and dissolution difficulties can often result in clinical usage of subpotent cyclophosphamide solutions.

Therefore, the main objective of the project culminating in the instant invention was to provide a cyclophosphamide dosage form with improved solubility characteristics and enhanced appearance, while maintaining stability comparable to the dry pre-mix composition. Unexpectedly, the unique lyophilized solid composition discovered has improved stability over the previous dry pre-mix composition.

Problems with unstable drug solutions have been handled previously by practitioners in the pharmaceutical arts by applying lyophilization, cf: L. Lachman, et al, "The Theory and Practice of Industrial Pharmacy", 2nd Ed., Lea & Febiger, Philadelphia, P.a., pp. 521–524 (1976); "Remington's Pharmaceutical Sciences", 15th Ed., Mack Publishing Co., Easton, P.a., pp. 1483–1485 (1975). The technique known as lyophilization is often employed for injectable pharmaceuticals which exhibit poor stability in aqueous solution. This process involves freeze drying, whereby ice is sublimed from frozen solutions leaving only the solid, dried components of the original liquid.

The particular advantages of lyophilization are that biologicals and pharmaceuticals which are unstable in aqueous solution yet relatively stable in the solid state can be processed and filled into dosage containers in solution, taking advantage of the relative ease of processing a liquid; dried without elevated temperatures, thereby eliminating adverse thermal effects; and then stored in the dry state in which there are relatively few stability problems. Additionally, freeze dried products are often more soluble and/or more rapidly solubilized, dispersions are stabilized, and products subject to degradation by oxidation or hydrolysis are protected.

Pharmaceuticals to be freeze dried are usually in aqueous solution ranging from 0.01 to 40% in concentration of total solids. Final moisture content of the dried product is generally below 1.0% although some products, mainly biologicals, may have a final moisture content which could range as high as about 10%. Usually, the improvement in stability of the lyophilizate, compared to the solution, is due to the absence of water in the pharmaceutical composition.

The active constituent of many pharmaceutical products, though, is present in such small quantity that if freeze-dried alone, it may not give a composition of suitable bulk and, in some cases, its presence would be hard to detect visually. Therefore, excipients are often added to increase the amount of solids present. In most applications it is desirable for the dried product cake to occupy essentially the same volume as that of the original solution. To achieve this, the total solids content of the original solution is usually about 10 to 25%. Among substances found useful for this purpose, often in combination, are sodium or potassium phosphates, citric acid, tartaric acid, gelatin, lactose and other carbohydrates such as dextrose, mannitol, and dextran; and on occasion, preservatives. Various excipients contribute appearance characteristics to the cake, such as whether dull and spongy or sparkling and crystalline, firm or friable, expanded or shrunken, and uniform or striated. Therefore, formulation of a composition to be freeze dried must include consideration not only of the nature and stability characteristics required during the liquid state, both freshly prepared and when reconstituted before use, but the characteristics desired in the final lyophilized cake. Additionally, for products to be reconstituted for parenteral usage, consideration must also be given to the pharmacological effects of excipients chosen. In some instances, there may even be chemical interaction between the active ingredient and one or more of the excipients during processing. This could, of course, result in reduced potency of the finished product.

For all the above reasons, it becomes apparent that selection of a suitable excipient or excipients for a pharmaceutical product containing a reactive, thermally labile, and inherently unstable ingredient such as cyclophosphamide is not an obvious process. Considerable testing, including drug assay, would be required, as in the instant case, for the development of such a composition. We surprisingly found that only the use of mannitol as the primary excipient gave a far superior lyophilizate compared to lyophilizates obtained using other excipients. Unexpectedly, we also discovered that a lyophilized cyclophosphamide solid composition containing about 4% moisture gave a product with superior thermal stability, compared to currently available dry powder premixes, lyophilized cyclophosphamide solid compositions with moisture levels of about 1% or less, or even cyclophosphamide itself.

SUMMARY OF THE INVENTION

This invention concerns an improved solid pharmaceutical composition and is based in part upon the discovery that a lyophilized cyclophosphamide-mannitol solid composition has improved thermal stability when it contains an amount of water approximately equimolar to the cyclophosphamide content taken as the anhydride. Of equal importance is the discovery that the desirable physical properties of the solid composition appear to be achieved only by using mannitol as the major excipient. Two processes have been developed which allow facile production of the solid composition in vials for packaging as unit dosage forms for reconstitution as sterile solutions.

DETAILED DESCRIPTION OF THE INVENTION

The therapeutically-active component of this invention, cyclophosphamide, is a well known and widely used anticancer agent. Cyclophosphamide chemically is 2-[bis-(2-chloroethyl)amino]tetrahydro2H-1,3,2-oxazaphosphorine-2-oxide monohydrate, shown in Formula I

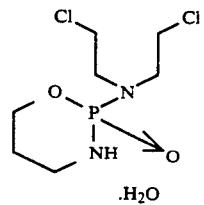

It is appreciated by the practitioner that the degree of reactivity desired for efficacy in an agent of this sort necessarily acts as a limit to its inherent stability in aqueous solution. Mainly for this reason, cyclophosphamide is compounded as a sterile dry powder mixture of cyclophosphamide monohydrate and NaCl for constitution with sterile water just prior to administration. Some instability of cyclophosphamide dry powder mixes can be evidenced by change in physical properties, e.g. decreased rate of dissolution, change in appearance, and the like, as well as loss of potency on storage. This deterioration becomes more pronounced on extended storage or on exposure of the powder mix to temperatures above about 90° F., a temperature not uncommon during commercial transportation or warehouse storage. Freshly prepared solutions made up from this powder mix can exhibit lowered potency due not only to prior degradation of the active ingredient but also through incomplete dissolution of the powder mix as well.

The instant invention has resulted from work undertaken to ascertain if physical properties, especially dissolution rate, could be improved in a lyophilized composition containing anhydrous cyclophosphamide.

Cyclophosphamide was thoroughly tested with those excipients compatible with parenteral administration to determine if a suitable lyophilizate cake could be formed by freeze-drying. Following the lyophilization process, the resulting cake was evaluated visually on its physical appearance using as desired criteria: original shape, no shrinkage or meltback, good coloration, homogeneity, firmness, and crystallinity. The dissolution rate was then tested and a global score of poor, fair, or good, based on the above criteria, was assigned, cf: Table 1.

TABLE 1

| Excipient Testing For Cake Formation | | |
|---|---|---|
| Excipient | Pre-lyophilization Solution: Concentration (% W/V) | Lyophilization Result |
| Lactose | 1.0, 2.0, 2.5, 3.3, 3.5, 5.0, 6.7, 8.0 | Poor cakes |
| Dextrose | 2.0, 2.5 | Poor cakes |
| Tartaric acid | 2.0 | Poor cake |
| Urea | 1.0, 2.0, 2.5 | Poor cakes |
| L-arginine | 0.5 | Poor cake |
| Polyvinyl-pyrrolidone (PVP) | 3.0 | Poor cake |
| $KH_2PO_4$ | 1.0 | Poor cake |
| $K_2HPO_4$ | 1.0 | Poor cake |
| $Na_2CO_3$ | 1.0 | Poor cake |
| $NaHCO_3$ | 1.0, 1.25, 1.5 | Poor to fair cakes |
| $NaHCO_3$ | 1.75, 2.0, 2.5 | Good cakes |
| Mannitol | 1.7, 2.0, 2.5, 3.0, 4.0, 5.0, 6.0, 7.0 | Good cakes |
| Mannitol | 10.0, 15.0 | Poor cakes |
| $CH_3CO_2K$ | 2.5, 3.0, 5.0 | Poor cakes |

Each solution for lyophilization contained 3.57% (W/V) cyclophosphamide monohydrate and an excipient or excipients. The solutions were prepared using Water for Injection and were filtered through a prefilter and a 0.22 μm filter membrane. The solutions were filled into 30 mL serum vials with a fill volume of 15 mL of solution per vial (the equivalent of 500 mg of anhydrous cyclophosphamide).

Prior to lyophilization, the filled vials were prechilled to 5° C. in a refrigerator. The vials were then frozen in the lyophilization chamber for approximately 2 hrs to a temperature of about −35° C. After cooling the condenser to about −60° C., the lyophilizer chamber was evacuated to approximately 50 millitorr. An initial shelf temperature of 0° C. was maintained for the first 14–16 hrs of the lyophilization cycle. The shelf temperature was then raised to 25° C. The cycle was completed when the product temperature stabilized near the shelf temperature, usually requiring 2–6 more hours, and the vacuum pressure reached equilibrium at a reading of approximately 100 millitorr. During lyophilization, product temperature was monitored using thermocouple probes placed inside several vials.

After the lyophilization process was completed, the material remaining in the vial was observed for color, appearance, texture, friability, and shrinkage from the original frozen volume. Also, each formulation was tested for its moisture loss on drying (4 hrs at 70° C. under vacuum) and its dissolution characteristics upon reconstitution with 25 mL of Sterile Water for Injection.

Unexpectedly, only two excipients from this group (Table 1) exhibited favorable cake-forming ability in the presence of cyclophosphamide. These two prototype formulations (containing $NaHCO_3$ or mannitol) retained their original shape, possessed suitable texture and appearance, and dissolved easily upon reconstitution with water. Most of the other excipient formulations were unsuitable due to poor quality cakes due mainly to shrinkage and/or poor dissolution. As can be seen from Table 1, only mannitol, at concentrations of 7% W/V or below, and sodium bicarbonate were initially found to be acceptable excipients in the cyclophosphamide lyophilization process. The formulations containing these two excipients dissolved easily within a few seconds upon reconstitution with water.

Further experimentation utilizing the same experimental procedure to investigate lyophilization results using mixed excipients demonstrated the surprising finding that fair to good lyophilizate cakes could be obtained only with mannitol compared to lactose or sodium bicarbonate as a primary excipient; cf: Table 2.

TABLE 2

| Primary Excipient (Concentration % W/V) | Secondary Excipient (Concentration % W/V) | Lyophilization Result |
|---|---|---|
| Lactose (2.0) | Mannitol (1.0, 1.5) | No cakes |
| Lactose (3.3) | Citric acid, anhyd. (1.0) | No cake |
| | $Na_2CO_3$ (1.0) | No cake |
| | $NaHCO_3$ (1.25) | No cake |
| $NaHCO_3$ (1.5) | NaCl (0.25) | Poor cake, shrinkage |
| | Glycine (0.25; 0.5) | Poor cakes, shrinkage |
| | $K_2HPO_4$ (0.5) | Poor cake, shrinkage |
| | Citric acid, anhyd. (0.5) | Poor cake, shrinkage |
| | Lactose (0.5, 1.0, 1.5) | Poor cakes, very fragile |
| $NaHCO_3$ (2.0) | Glycine (0.5) | Poor cake, very fragile |
| | Na citrate (0.5) | Poor cake, very fragile |
| Mannitol (2.0) | Na ascorbate (0.33) | Poor cake, shrinkage |
| | Na acetate (0.33) | Poor cake, slow dissolution |
| | Na citrate (0.33) | Poor cake, shrinkage |
| | $Na_2CO_3$ (0.5) | No cake |
| | $NaHCO_3$ (0.5) | No cake |
| | PVP (1.0) | Fair cake, sl. shrinkage |
| Mannitol (2.5) | Na citrate (0.33, 0.5, 0.67) | Poor cakes, shrinkage |
| | L-arginine (0.5) | Poor cake, slow dissolution |
| | Glycine (0.5, 1.0) | Poor cakes, unhomogenous |
| | PVP (0.5, 1.0) | Fair to good cakes |
| Mannitol (3.0) | Glycine (0.5) | Fair cake, sl. shrinkage |
| | Na citrate (0.33) | Good cake |

Most of the compositions listed in Table 2 exhibited some ability to form lyophilizate cakes except those in which lactose was the primary excipient; however, most of the resulting cakes were of poor quality due to friability, shrinkage and/or poor dissolution. The lyophilizates containing various secondary excipients with sodium bicarbonate were of poorer quality than the lyophilizates with sodium bicarbonate as the only excipient. One formulation containing mannitol as the primary excipient and sodium citrate and a second formulation containing mannitol as the primary excipient and polyvinylpyrrolidone (PVP) formed acceptable lyophilizates that were firm, homogenous cakes with minimum friability and shrinkage. These two combination excipient products dissolved easily in a few seconds upon reconstitution with water. These selected lyophilized solid compositions all had low moisture levels, as measured by loss on drying, on the order of about 2% or less. While considerable improvement of the dissolution properties and physical appearance was achieved with these low moisture cyclophosphamide lyophilizates, six-week stability testing indicated that these lyophilized solid compositions were heat sensitive and, in fact, much less stable than the existing sodium chloride/cyclophosphamide monohydrate dry powder premixture.

It was unexpectedly discovered, however, that humidification of these low moisture lyophilized cyclophosphamide solid compositions ("dry" lyophilizates) could be easily and reproducibly effected by subjecting them to an air atmosphere of about 60 to 80% relative humidity at about 25° C. in a closed container for 1–2 days. Under these conditions, a state of equilibrium could be achieved in which the moisture gained on a molar basis was approximately equivalent to the anhydrous cyclophosphamide content of the lyophilizate. The improved dissolution characteristics found in the "dry" cyclophosphamide lyophilizates remained essentially unchanged upon humidification. Stability testing of the humidified solid compositions ("hydrated" lyophilizates) demonstrated that those compositions containing mainly mannitol as the excipient were unexpectedly superior, compared with the sodium bicarbonate excipient compositions in maintaining minimal dissolution times, cf: Table 3.

TABLE 3

Comparative Stability Testing of "Hydrated" Solid Lyophilizates: Mannitol as excipient vs NaHCO₃ as excipient

| Storage Temperature | Time (Wks) | Dissolution Times (sec) Mannitol | Dissolution Times (sec) NaHCO₃ |
|---|---|---|---|
| 40° | 3 | ~20 | >180 |
|  | 6 | ~60 | >180 |
|  | 12 | ~60 | ~120 |
| 35° | 3 | ~20 | >180 |
|  | 6 | ~60 | >180 |
|  | 12 | ~60 | ~120 |
| 25° | 6 | ~60 | >180 |
|  | 12 | ~60 | >180 |

Preferred solid compositions of the instant invention are comprised of about 20 parts by weight of cyclophosphamide, taken as the anhydrous form, about 1¼-2 parts by weight of water and from about 10-40 parts by weight of excipient which is primarily mannitol. Most preferred compositions are comprised of about 20 parts by weight of cyclophosphamide, taken as the anhydride, about 1½ parts by weight of water and about 15 parts by weight of excipient consisting essentially of mannitol.

These solid compositions may be prepared by either of two methods. The first method, of which one embodiment as mentioned hereinabove, involved lyophilization and humidification. Common to both methods is preparation of a sterile solution for lyophilization. A typical solution is composed of about 1 part by weight excipient which is mainly mannitol, about 1.5 parts by weight cyclophosphamide (as the monohydrate), and about 40 parts water. In order to obtain optimal results with the lyophilizate composition this solution should not contain much more than about 4% cyclophosphamide content. Continuing with the first method, this solution is aseptically filled into suitable containers and then lyophilized to a "dry" lyophilizate cake which has a moisture content on the order of about 2% or less. This lyophilization is done in a short period of time (~24 hrs) at a lyophilization chamber pressure of about 100 to 500 millitorr using a very cold condenser temperature (about −60° C.) and a warm shelf temperature (about 20°-25° C.). This typical "dry" lyophilizate is then humidified to give a "hydrated" lyophilizate containing approximately 4% moisture. With humidification at atmospheric pressure, further water pick-up essentially stops at this point giving the stable "hydrated" lyophilizate solid composition of the instant invention. The amount of water taken up is approximately equimolar ranging to about 30% excess compared with the cyclophosphamide (on an anhydrous basis) present in the cake. While the humidification can be done at approximately atmospheric pressure, the time required for complete humidification is considerably shortened (to at least a third or less) when done under reduced pressure. By reduced pressure is meant a pressure of about 0.1 to 25 torr. A unit of 1 torr is equivalent to 1/760 standard atmospheric pressure.

A second method of obtaining the desired lyophilized solid composition involves lyophilizing the sterile solution directly using a longer lyophilization cycle (~48 hrs). This method, done more slowly under milder conditions, requires adjustment of certain parameters of the lyophilization process such as shelf temperature, and condenser temperature during the process of drying. This second lyophilization process comprises 2 stages of freeze-drying done under a 500 millitorr chamber pressure. The first stage of freeze-drying is done with a low condenser temperature of about −60°, and a shelf temperature at about 10° C. The second stage of freeze-drying requires raising the condenser temperature to about −30° C. and lowering the shelf temperature to about −10° C.

These lyophilized cyclophosphamide solid compositions may be provided in single dose container forms by aseptically filling suitable containers with the sterile pre-lyophilization solution to a prescribed cyclophosphamide content; preparing the desired lyophilized solid composition, using either of the two methods described hereinabove; and then hermetically sealing the single dose container. It is intended that these filled containers will allow rapid dissolution of the solid composition upon reconstitution with water in situ giving an appropriate sterile solution of desired cyclophosphamide concentration for administration. By suitable containers is meant a container capable of maintaining a sterile environment such as a vial capable of being hermetically sealed by a stopper means. Additionally, suitable containers implies appropriateness of size, considering the volume of solution to be held upon reconstitution of the lyophilized composition; and appropriateness of container material, generally Type I glass. The stopper means employed, e.g. sterile rubber closures or an equivalent, should be understood to be that which provides the aforementioned seal but which also allows entry for the purpose of introduction of diluent, e.g. sterile water, for reconstitution of the desired cyclophosphamide solution. These and other aspects of the suitability of containers for pharmaceutical products such as those of the instant invention are well known to those skilled in the practice of pharmaceutical arts.

While the physical properties, such as appearance and particularly dissolution time, were improved in the instant solid compositions, thereby achieving one objective of the invention, we unexpectedly found that these instant solid compositions also possessed improved thermal stability compared with currently known dry powder premix formulations as well as cyclophosphamide itself. In practice, expectation for enhancement of chemical stability by lyophilization relates to a comparison of the lyophilizate solid with the solution form of the pharmaceutical composition. In contrast, the instant compositions demonstrate enhanced chemical stability between solid dosage forms, cf: Table 4.

TABLE 4

Comparative Chemical Stabilities for "Hydrated" Cyclophosphamide/Mannitol Lyophilizate and CYTOXAN ® for Injection (Powder Premix)

| Storage Temperature | Time (Wks) | Potency (% of Zero-time) Lyophilizate | Potency (% of Zero-time) CYTOXAN ® |
|---|---|---|---|
| 50° | 1 | 31 | 31 |
| 45° | 1 | 94 | 80 |
|  | 2 | 76 | 42 |
| 40° | 1 | 100 | 98 |
|  | 3 | 101 | 85 |
|  | 6 | 99 | 33 |
|  | 12 | 98 | 2 |
| 35° | 3 | 101 | 105 |
|  | 6 | 100 | 98 |
|  | 12 | 100 | 98 |
|  | 26 | 98 | 85 |
| 25° | 6 | 100 | 101 |
|  | 12 | 100 | 100 |

TABLE 4-continued

Comparative Chemical Stabilities for "Hydrated"
Cyclophosphamide/Mannitol Lyophilizate and
CYTOXAN ® for Injection (Powder Premix)

| Storage Temperature | Time (Wks) | Potency (% of Zero-time) | |
|---|---|---|---|
| | | Lyophilizate | CYTOXAN ® |
| | 26 | 100 | 103 |

It is recognized by practitioners in the pharmaceutical arts that the use of elevated storage temperatures for shorter time periods is standard practice in obtaining comparative stability data. As can be seen in Table 4, the "hydrated" cyclophosphamide/mannitol lyophilized solid composition possesses greater thermal stability than the current CYTOXAN ® for Injection dry powder formulation.

Short term comparative stability studies have also been made using the "hydrated" cyclophosphamide/mannitol lyophilized solid composition, a cyclophosphamide monohydrate/mannitol dry powder blend (not lyophilized), CYTOXAN ® for Injection dry powder premix, and pure cyclophosphamide monohydrate. These studies at a storage temperature of 40° C. gave the results summarized in Table 5.

TABLE 5

Comparative Stabilities at 40° C. for:
A. "Hydrated" Cyclophosphamide/Mannitol Lyophilizate
B. Cyclophosphamide Monohydrate/Mannitol Powder Blend
C. CYTOXAN ® for Injection (Powder Premix)
D. Cyclophosphamide Monohydrate

| Time (Wks) | Potency (% of Zero-time) | | | | Physical Appearance | | | |
|---|---|---|---|---|---|---|---|---|
| | A | B | C | D | A | B | C | D |
| 3 | 104 | 96 | 93 | 95 | un-changed | sl. melted | sl. melted | un-changed |
| 6 | 102 | 57 | 39 | 37 | un-changed | melted | melted | melted |
| 12 | 101 | 42 | 4 | — | un-changed | melted | melted | — |

As these tabular results show, the "hydrated" cyclophosphamide/mannitol lyophilized solid composition demonstrates superior thermal stability as well as maintenance of initial physical appearance. In summary, the "hydrated" cyclophosphamide/mannitol lyophilized solid composition shows unexpected improved stability, superior solubility characteristics, and enhanced appearance when compared with other powder premix formulations of cyclophosphamide monohydrate and cyclophosphamide monohydrate alone. These improved characteristics are indicative of a superior pharmaceutical solid composition.

The following examples describe in detail methods for preparation of a solid composition of the present invention. It will be apparent to those skilled in the art that many modifications, both of methods and materials may be practiced without departing from the purpose and intent of this disclosure. From the foregoing description and the following examples, it is believed that one skilled in the art is able to use the invention to the fullest extent.

EXAMPLE 1

Lyophilization—Humidification Process

An aqueous solution is typically prepared by dissolving mannitol (375 g) and cyclophosphamide monohydrate (535 g) in 13 liters of Water for Injection. Additional Water for Injection is added in order to bring the final volume of this solution to 15 liters. The solution is first passed through a sterile prefilter and then a sterile 0.22 μm pore size membrane filter, following which the sterile solution is then aseptically filled into sterile 30 mL glass vials. Each vial is filled with 15.0 mL solution (containing the equivalent of 500 mg anhydrous cyclophosphamide) and then sterile rubber closures are aseptically inserted in the lyophilization position. These filled vials are placed in suitable lyophilization equipment and cooled as quickly as possible to a temperature of about −35° C.

The lyophilizer condenser is then cooled to about −60° C. and the lyophilization chamber is evacuated to a pressure of approximately 500 millitorr. Shelf heat is set at +20° C. to begin the drying process. Following about 15-20 hours of primary drying, the shelf temperature is raised in order to bring the product temperatures to near +25° C. provided that the product temperature thermocouples have reached +15° to +18° C. and the lyophilization chamber pressure is not more than 500 millitorr at that point. Lyophilization is then continued until a final product temperature of +22° to 24° C. with a chamber pressure of not more than about 200 millitorr, is reached. Depending on the capacity of the lyophilization equipment and the product batch size, the total lyophilization time will vary but is generally in the range of 24-36 hours. Following completion of the lyophilization process, the high vacuum is relieved by the aseptic introduction of sterile air and/or nitrogen having 80% relative humidity at room temperature. An aseptic environment is maintained during this rehydration process which is complete within approximately 18-24 hours at atmospheric pressure. At this point, the vials are closed by aseptically seating the lyophilization stoppers into the vials by mechanical collapse of the shelves.

A preferred method of humidification involves introducing water vapor into the lyophilization chamber while it remains under reduced pressure. With the chamber at about 25° C. and with a closed vacuum (pump off) of about 100-200 millitorr, a quantity of sterile water is vaporized into the chamber during which time the pressure may increase to about 25 torr. The quantity of sterile water used depends on the size of the lyophilization equipment being used as well as the product batch size. Typically, for 180 vials of the size and content described hereinabove and with a lyophilization chamber volume of approximately 125 liters, the amount of water used is on the order of 9 mL. The introduction of water is accomplished by establishing a closed system and bleeding in the water vapor issuing from a reservoir of liquid water kept at about 60°-80° by external heating. Boiling chips are used to prevent bumping and the introduction of water is completed within approximately 45 minutes. The internal chamber pressure during this "vacuum humidification" process varies from about 0.1 to 25 torr with the introduction of the water vapor. Total time of humidification using this method generally requires about 2-6 hours, again depending on lyophilization equipment size and product batch size. After humidification, the remaining vacuum is relieved by introduction of sterile air and/or nitrogen and the vials are closed by aseptically seating the lyophilization stoppers into the vials by mechanical collapse of the shelves.

EXAMPLE 2

Direct Lyophilization Process

Utilizing the filled vials with stoppers as described above in Example 1, the lyophilization equipment is loaded and the vials cooled as rapidly as possible to a temperature of about $-35°$ C. For stage 1 of this freeze-drying process the lyophilizer condenser is cooled to about $-60°$, the lyophilization chamber is evacuated to approximately 500 millitorr, and the shelf is held at a temperature on the order of $+10°$ C.

When the product temperature (measured by thermocouple) reaches about $-12°$ C., generally after about 10-12 hours, adjustments are made for the second stage of freeze-drying. The shelf temperature is lowered to about $-10°$ C. and the condenser temperature is raised to about $-30°$ C. Depending on capacity of the equipment being used and the size of the product batch, approximately 36-48 hours of total lyophilization time is required in order to reach equilibrium in the chamber and for the product to reach the desired final product temperature, as measured by thermocouple, of about $-10°$ C. When this second stage of freeze-drying of the lyophilization process is complete, the vacuum is relieved by the aseptic introduction of sterile nitrogen and/or air. The containers are then closed as in Example 1 above.

The lyophilized solid compositions resulting from use of the processes outlined above in Examples 1 and 2 contain, within ±10%, 500 mg cyclophosphamide (on the anhydrous basis) and 375 mg of mannitol. While the intended amount of water is 35 mg (equimolar with 500 mg of anhydrous cyclophosphamide), in actual practice this amount varies from about $-10\%$ to about $+30\%$.

The sealed vials described in Examples 1 and 2 are intended for use as single dose formulations following reconstitution with about 25 mL of Water for Injection. The reconstituted solutions may be administered either parenterally or orally. Additional single dose formulations are shown in Table 6. The values listed for volumes and weights are the nominal values and may be expected to vary as mentioned hereinabove.

TABLE 6

Additional Single Dose Formulations

| Example No. | Lyophilizate Compositions | | | Volume of Water for Reconstitution (mL) |
|---|---|---|---|---|
| | Cyclophosphamide (mg, anhydrous basis) | Mannitol (mg) | H$_2$O (mg) | |
| 3 | 100 | 75 | 7 | 5 |
| 4 | 200 | 150 | 14 | 10 |
| 5 | 1000 | 750 | 70 | 50 |
| 6 | 2000 | 1500 | 140 | 100 |

FURTHER DETAILED DESCRIPTION OF THE INVENTION

A number of additional examples of solid compositions of the instant invention similar to those defined hereinabove have been prepared. These additional examples of the lyophilized pharmaceutical solid compositions serve to extend the range of the excipient, comprised of mannitol, upward to about 85 parts by weight in the composition. Examples of the solid compositions of the instant invention disclosed hereinbefore contain an excipient range of from about 10 to 40 parts in the final composition. These compositions resulted from lyophilization of solutions containing about 3.33% W/V cyclophosphamide, on an anhydrous basis, and having mannitol concentrations of from 1.7 to 7.0% W/V. Lyophilization of these solutions (cf: Table 1, page 9) resulted in good and acceptable lyophilizate cakes as evaluated according to the criteria of physical appearance (original shape, no shrinkage or meltback, good coloration, homogeneity, firmness, and crystallinity) and an acceptable dissolution rate upon reconstitution. Results obtained by the lyophilization of solutions containing 3.33% W/V cyclophosphamide but with mannitol concentrations of 10 or 15% produced poor or unacceptable lyophilizate cakes when judged by the above criteria. These cakes were not homogeneous, did not retain their original shape, and/or did not dissolve rapidly upon reconstitution.

Continuing study was directed to determine the upper boundary of the range of the mannitol excipient which could be achieved in an acceptable solid composition of the instant invention. Production of these high mannitol content solid compositions requires some alteration of the processes as previously described, particularly in regard to the initial pre-lyophilization solution employing a lower cyclophosphamide concentration and progressively larger amounts of water. Examples of these higher mannitol excipient content compositions are shown below in Table 7.

TABLE 7

| Pre-lyophilization Solution Concentration (% W/V) | | Solution Fill Volume (mL) for 500 mg Cyclophosphamide | Lyophilizate Composition (parts by weight) |
|---|---|---|---|
| Cyclophosphamide (CY) | Mannitol (MAN) | | |
| 3.33 | 7.00 | 15.00 | CY 20, MAN 42, H$_2$O 1.4 |
| 2.67 | 7.00 | 18.75 | CY 20, MAN 52.5, H$_2$O 1.4 |
| 2.22 | 7.00 | 22.50 | CY 20, MAN 63, H$_2$O 1.4 |
| 1.90 | 7.00 | 26.2 | CY 20, MAN 73.5, H$_2$O 1.4 |
| 1.67 | 7.00 | 30.00 | CY 20, MAN 84, H$_2$O 1.4 |

To summarize; the solid compositions of the present application have the following ingredients and concentrations:

cyclophosphamide—about 19 to 64% by weight,
water—about 1 to 5% by weight,
mannitol—about 32 to 80% by weight,
preferred compositions:
cyclophosphamide—about 32 to 64% by weight,
water—about 2 to 5% by weight,
mannitol—about 32 to 66% by weight; and
the most preferred composition:
cyclophosphamide—about 55% by weight,
water—about 4% by weight,
mannitol—about 41% by weight.

All of the above solid compositions possess the characteristics required for the improved solid compositions of the present invention. However, since lowering the cyclophosphamide concentration in the pre-lyophilization solution, in effect, requires the removal of more water during lyophilization, the process requires more time and is therefore, less efficient and more expensive. Thus, while lowering the cyclophosphamide concentration in the pre-lyophilization solution, containing mannitol at the 7.0% W/V level, has no detrimental effect on the quality of the final compositions, the decreased efficiencies in their production render them less preferred, though still operable, than the original compositions containing a final mannitol content of from about 10 to about 40 parts by weight.

What is claimed is:

1. A hydrated lyophilizate composition for reconstitution with water with improved stability and enhanced appearance comprising about 100 parts by weight of cyclophosphamide, taken as the anhydride, from about 6¼ to about 10 parts by weight of water and from about 50 to about 75 parts by weight of sodium bicarbonate.

2. A hydrated lyophilizate composition for reconstitution with water with improved stability and enhanced appearance comprising cyclosphosphamide, sodium bicarbonate in an amount sufficient to form a lyophilized cake retaining its original shape and capable of easy dissolution on reconstitution with water, and which has been rehydrated in order to impart improved thermal stability to the cyclophosphamide.

* * * * *